(12) United States Patent
Kuo et al.

(10) Patent No.: US 8,598,343 B2
(45) Date of Patent: Dec. 3, 2013

(54) PROCESS FOR PREPARING A 2-ALKYNYL SUBSTITUTED 5-AMINO-PYRAZOLO-[4,3-E]-1,2,4-TRIAZOLO[1,5-C]PYRIMIDINE

(75) Inventors: Shen-Chun Kuo, Union, NJ (US); Yonggang Chen, Scotch Plains, NJ (US); Jeffrey M. Eckert, Hazlet, NJ (US); William W. Leong, Westfield, NJ (US); Nanfei Zou, Cranford, NJ (US); Gabriel C. Kuklis, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/389,029

(22) PCT Filed: Aug. 3, 2010

(86) PCT No.: PCT/US2010/044212
§ 371 (c)(1),
(2), (4) Date: May 16, 2012

(87) PCT Pub. No.: WO2011/017299
PCT Pub. Date: Feb. 10, 2011

(65) Prior Publication Data
US 2012/0220769 A1 Aug. 30, 2012

Related U.S. Application Data

(60) Provisional application No. 61/232,144, filed on Aug. 7, 2009.

(51) Int. Cl.
*C07D 491/00* (2006.01)
(52) U.S. Cl.
USPC .......................................... 544/251
(58) Field of Classification Search
USPC .......................................... 544/251
See application file for complete search history.

(56) References Cited

U.S. PATENT DOCUMENTS 6,897,217 B2   5/2005   Neustadt et al.
7,223,861 B2 *  5/2007   Kuo et al. ............... 544/251
7,572,802 B2   8/2009   Boyle et al.

OTHER PUBLICATIONS

Abramovitch. Chemistry of Heterocyclic Compounds, vol. 14, Interscience Publishers, Inc. 1974.*

* cited by examiner

*Primary Examiner* — Noble Jarrell
*Assistant Examiner* — Laura Daniel
(74) *Attorney, Agent, or Firm* — H. Eric Fischer; John C. Todaro

(57) ABSTRACT

A process for preparing 7-[2-[4-(6-fluoro-3-methyl-1,2-benzisoxazol-5-yl)-1-piperazinyl]ethyl]-2-(1-propynyl)-7H-pyrazolo-[4,3-e]-[1,2,4]-triazolo[1,5-c]pyrimidin-5-amine, intermediates useful in that process, and processes for preparing said intermediates are disclosed.

5 Claims, No Drawings

PROCESS FOR PREPARING A 2-ALKYNYL SUBSTITUTED 5-AMINO-PYRAZOLO-[4,3-E]-1,2,4-TRIAZOLO[1,5-C]PYRIMIDINE

CROSS REFERENCE TO RELATED APPLICATIONS

This application is the National Stage of International Application No. PCT/US2010/044212 filed on Aug. 3, 2010, which claims the benefit under 35 U.S.C. 119(e) of U.S. Provisional Application No. 61/232,144 filed Aug. 7, 2009, each of which applications are incorporated by reference as if fully set forth herein.

FIELD OF THE INVENTION

The present invention relates to a process for preparing 7-[2-[4-(6-fluoro-3-methyl-1,2-benzisoxazol-5-yl)-1-piperazinyl]ethyl]-2-(1-propynyl)-7H-pyrazolo-[4,3-e]-[1,2,4]-triazolo[1,5-c]pyrimidin-5-amine, to intermediates useful in that process, and to processes for preparing said intermediates.

BACKGROUND

7-[2-[4-(6-Fluoro-3-methyl-1,2-benzisoxazol-5-yl)-1-piperazinyl]ethyl]-2-(1-propynyl)-7H-pyrazolo-[4,3-e]-[1,2,4]-triazolo[1,5-c]pyrimidin-5-amine (the compound of Formula I) is an adenosine $A_{2a}$ receptor antagonist useful in the treatment of central nervous system disorders including movement disorders, e.g., Parkinson's Disease, Extra-Pyramidal Syndrome, restless legs syndrome, essential tremor and Huntington's Disease; attention disorders, e.g., attention deficit hyperactivity disorder, cognitive impairment and negative symptoms of schizophrenia; and to other central nervous system diseases such as depression, stroke and psychoses. U.S. Pat. No. 6,897,217 and US 2007/0072867, the disclosures of which are herein incorporated by reference, relate to the compound of Formula I generically and specifically, respectively.

U.S. Pat. No. 6,897,217 discloses three general methods for preparing 2-alkynyl-substituted 5-amino-pyrazolo[4,3-e]-1,2,4-triazolo-[1,5-c]pyrimidines shown in the following Schemes A to C. A specific method for preparing the compound of Formula I disclosed in US 2007/0072867 is shown in Scheme D.

Scheme A

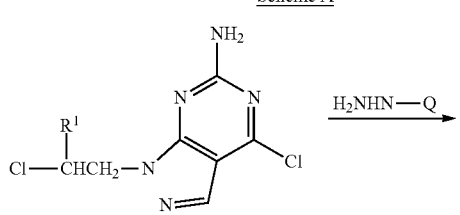

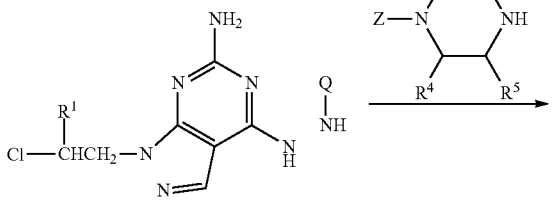

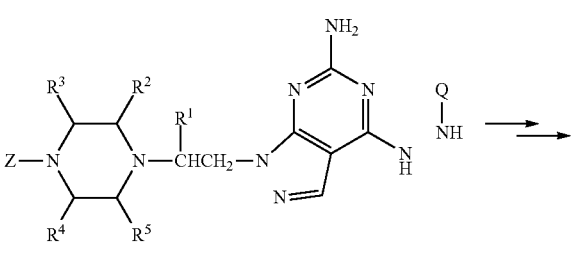

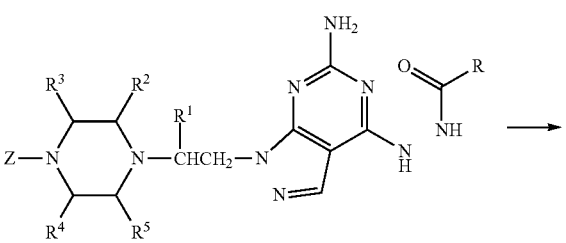

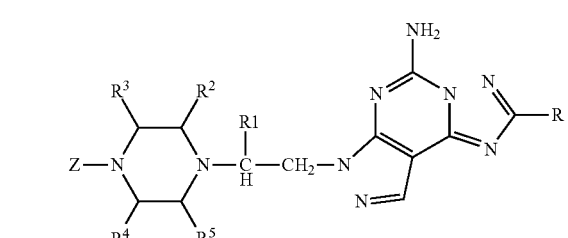

Scheme B

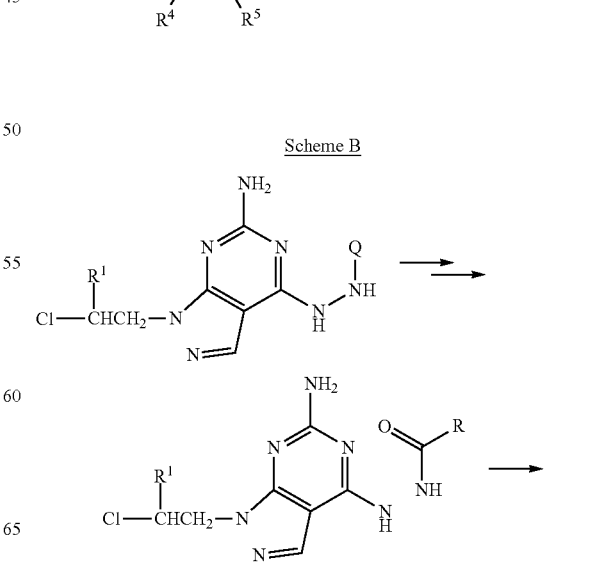

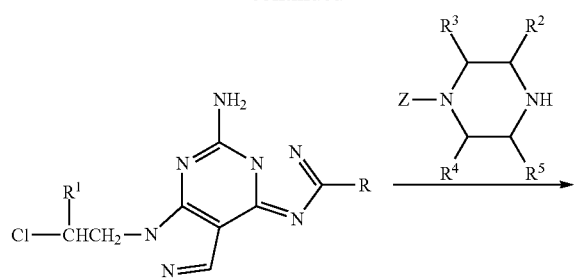
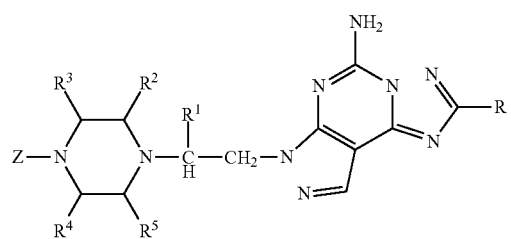
Scheme C
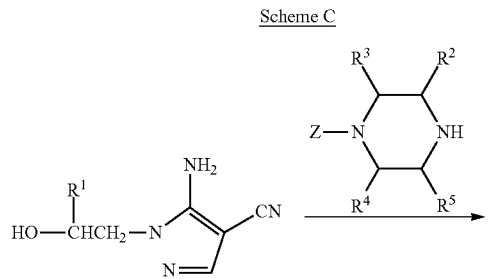
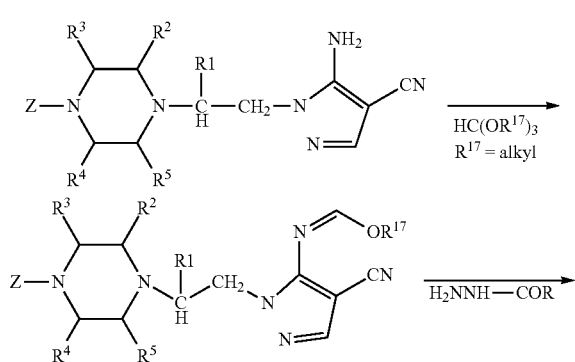
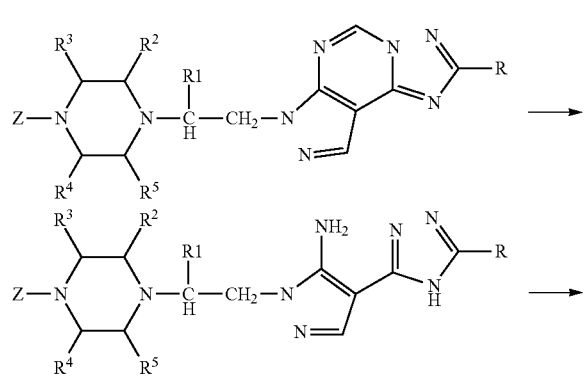
Scheme D
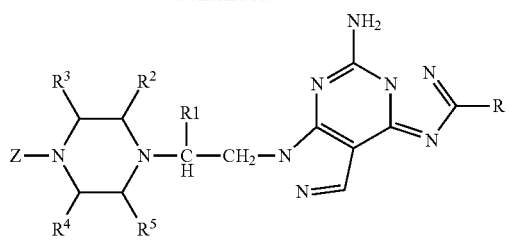
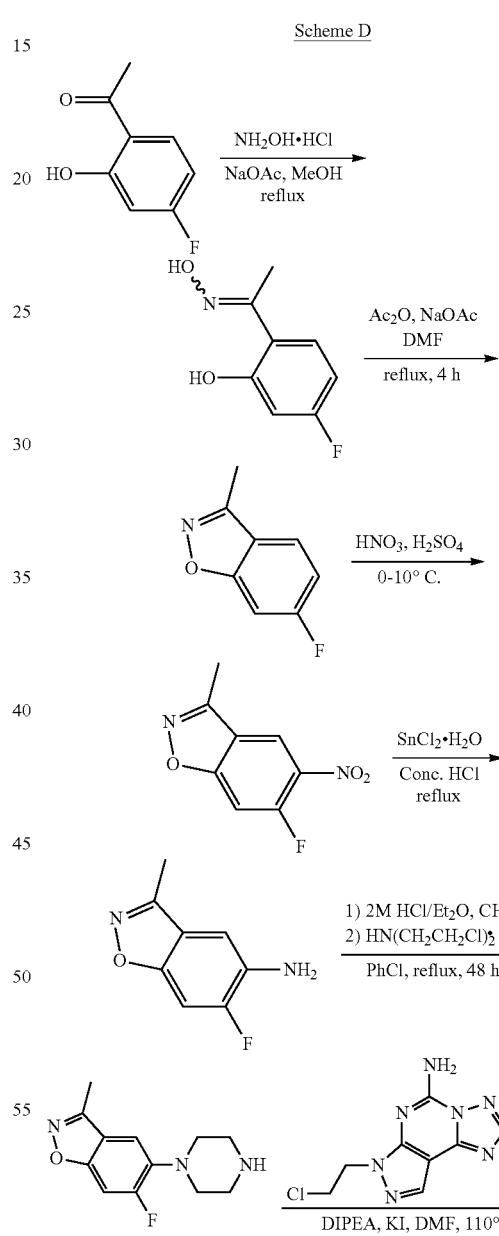
Processes for preparing 5-amino-pyrazolo-[4,3-e]-1,2,4-triazolo[1,5-c]pyrimidines substituted at the 2-position by, for example, a furanyl group are disclosed in U.S. Pat. No. 6,630,475 and U.S. Pat. No. 7,223,861.

SUMMARY OF THE INVENTION

The present invention relates to a process for preparing the compound having the structural Formula I

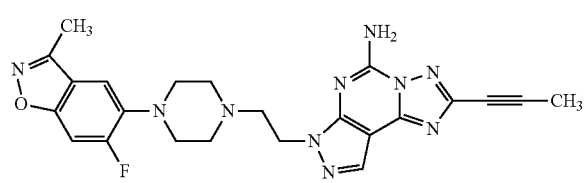

I comprising (i) condensing compounds II and III to obtain compound IV:

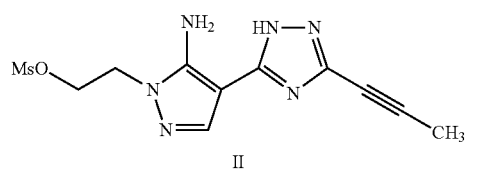

II

+

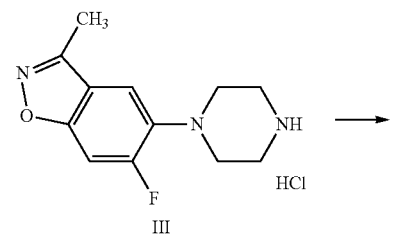

III

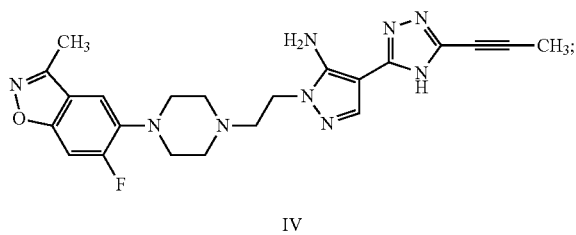

IV (ii) cyclizing compound IV to obtain compound I; and (iii) optionally purifying the product of step (ii).

The intermediate compound of formula II is prepared by the process comprising:

(a) treating compound V with triethyl orthoformate to obtain imidate VI:

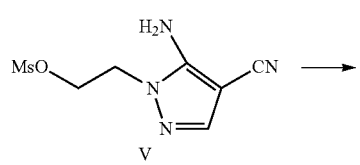

V

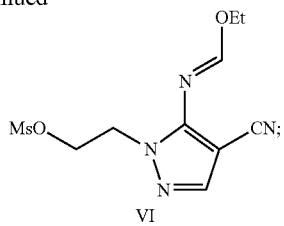

VI (b) condensing imidate VI with 2-butynoylhydrazine p-toluenesulfonate (VII) to obtain the adduct compound VIII:

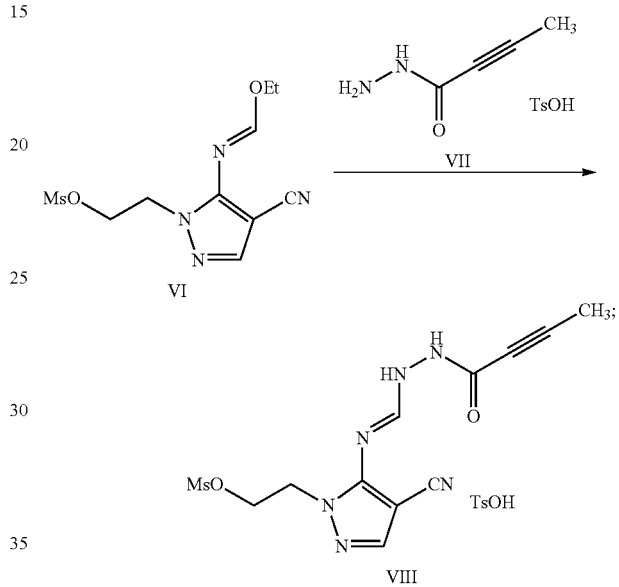

(c) cyclizing and dehydrating compound VIII with N,O-bistrimethylsilyl acetamide to obtain the 2-propynyl-substituted compound IX:

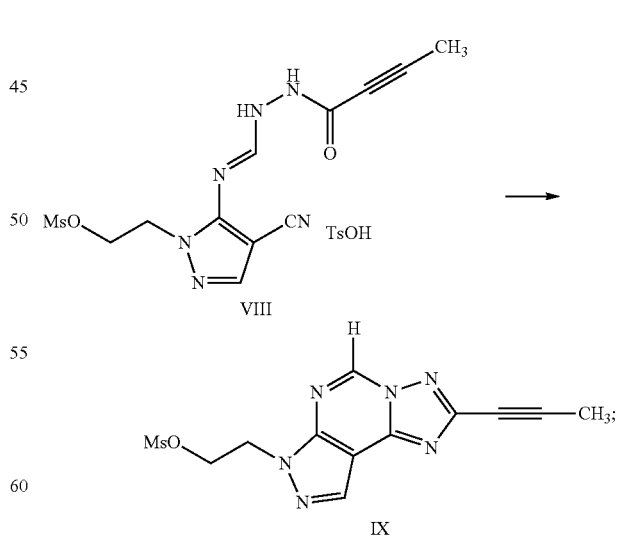

and (d) hydrolyzing compound IX to obtain compound II.

The intermediate compound of formula III is prepared by the processes comprising:

Method A:

(a) reacting 5-amino-6-fluoro-3-methyl-1,2-benzisoxazole (X) with bis(2-chloroethyl)amine in the presence of a base to obtain the compound III:

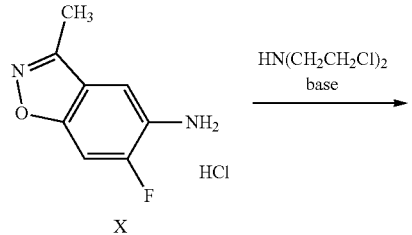

and (b) isolating compound III from the reaction mixture of step (a) by the addition of an anti-solvent; and Method B:

(a) treating the acetophenone XII with hydroxylamine hydrochloride to obtain the corresponding oxime (XIII)

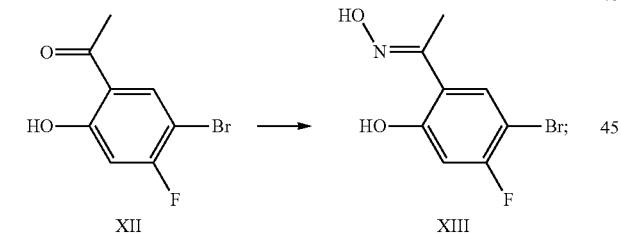

(b) cyclizing the oxime XIII to the benzisoxazole XIV

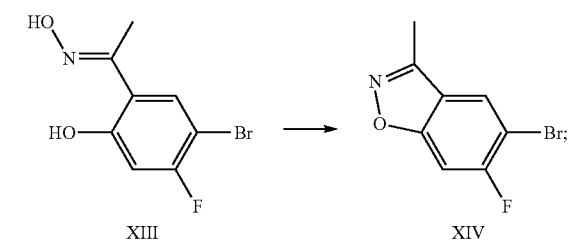

(c) converting the benzisoxazole XIV to an organozinc reagent and coupling it with a protected piperazine in the presence of a copper catalyst to obtain the compound XV

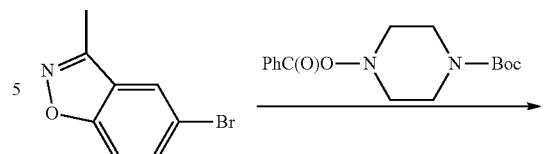

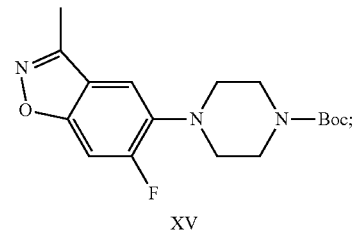

and (d) removing the protecting group on compound XV and converting it to the HCl salt to obtain compound III.

The following processes for preparing novel intermediates are claimed:

The process for preparing compound IV comprising condensing compounds II and III:

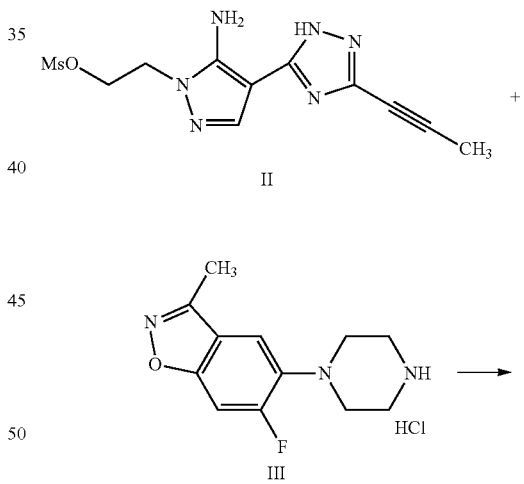

The process for preparing compound III comprising reacting 5-amino-6-fluoro-3-methyl-1,2-benzisoxazole (X) with bis(2-chloroethyl)amine in the presence of a base:

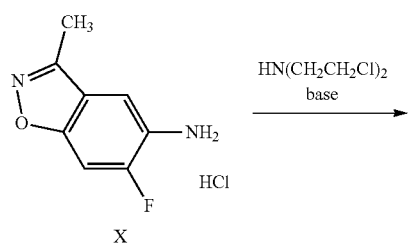

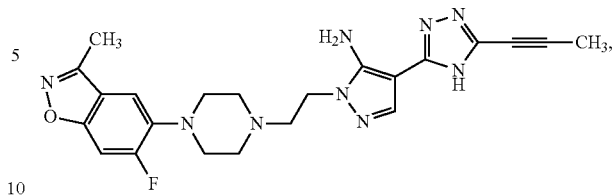

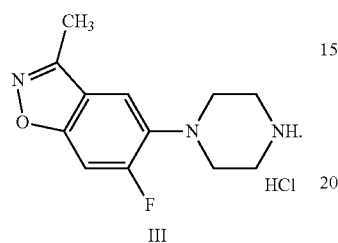

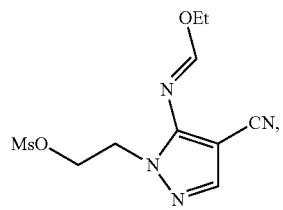

The process of isolating compound III from the reaction mixture comprising adding an antisolvent to the reaction mixture.

The process of preparing compound XV comprising converting the benzisoxazole XIV to an organozinc reagent and coupling it with a protected piperazine in the presence of a copper catalyst:

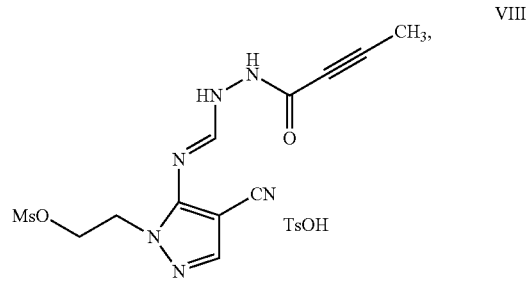

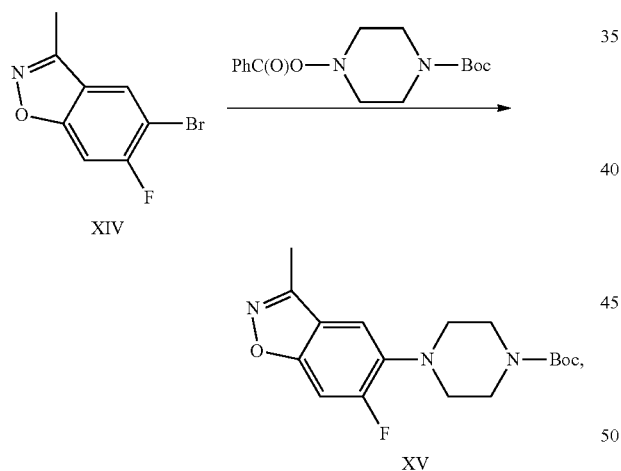

followed by removing the protecting group on compound XV and converting it to the HCl salt.

The following novel intermediates useful in the preparation of the compound of Formula I are claimed:

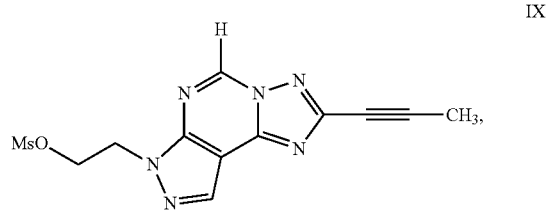

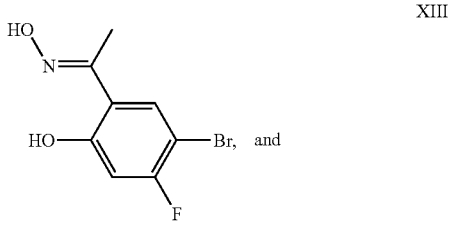

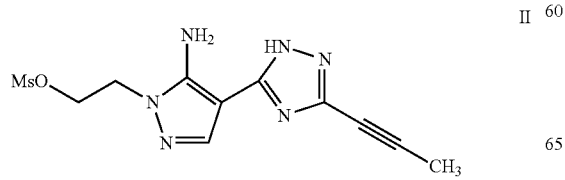

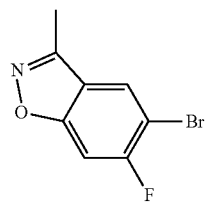

DETAILED DESCRIPTION

In one embodiment of the invention, the process for preparing the compound of Formula I

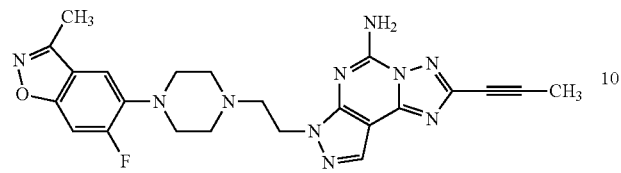

comprises:

(1) Preparing Compound II

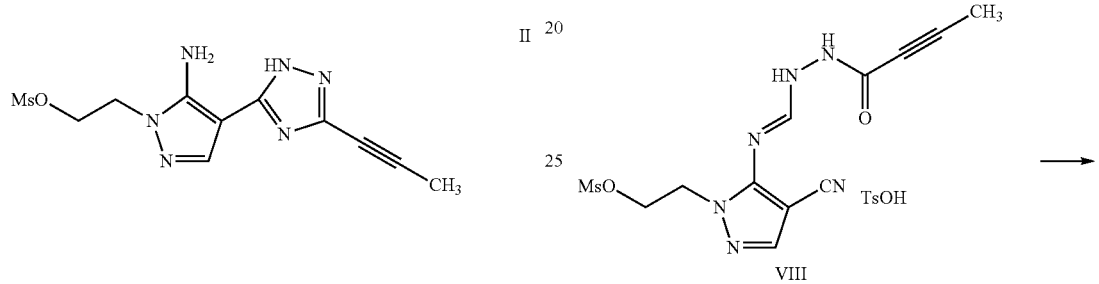

by (a) treating compound V with triethyl orthoformate to obtain imidate VI:

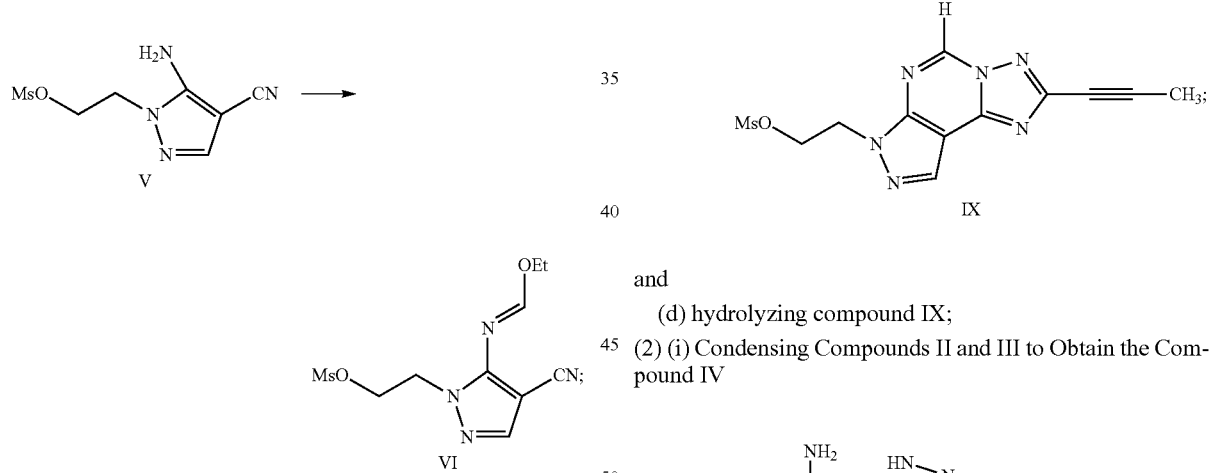

(b) condensing imidate VI with 2-butynoylhydrazine p-toluenesulfonate (VII) to obtain the adduct compound VIII:

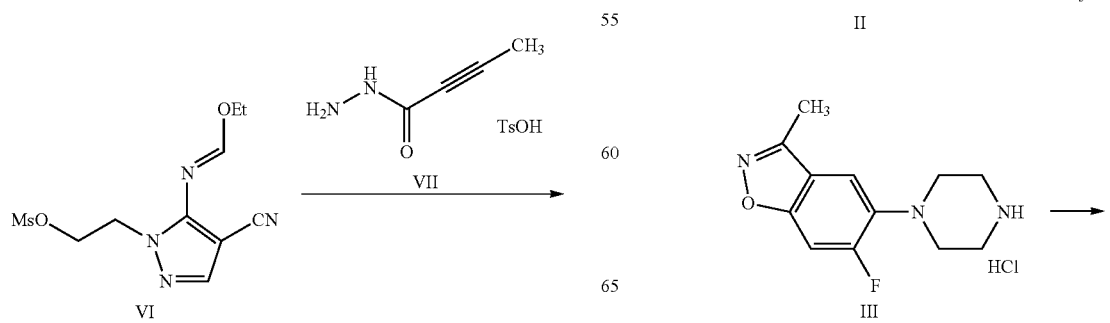

(c) cyclizing and dehydrating compound VIII with N,O-bistrimethylsilyl acetamide to obtain the 2-propynyl-substituted compound IX:

and
(d) hydrolyzing compound IX;
(2) (i) Condensing Compounds II and III to Obtain the Compound IV -continued

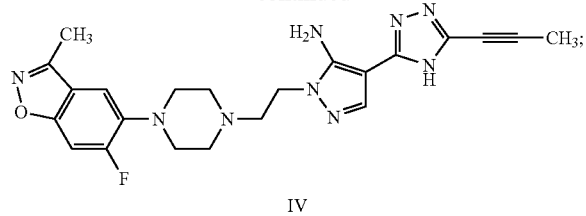

IV (ii) cyclizing compound IV to obtain compound I; and
(iii) purifying the product of step (ii).

In another embodiment of the invention, the process for preparing the compound of Formula I

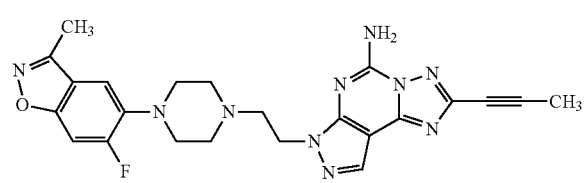 [SMILES: CC#Cc1nc2c3cnn(CCN4CCN(c5cc6c(C)noc6cc5F)CC4)c3nc(N)n2n1]

comprises:
(1) Preparing Compound II

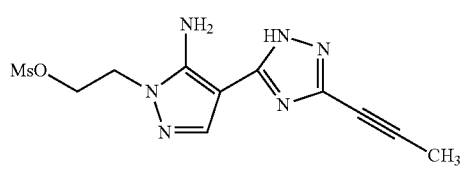 [SMILES: CC#Cc1n[nH]c(-c2cnn(CCOS(C)(=O)=O)c2N)n1]

by
(a) treating compound VI with triethyl orthoformate to obtain imidate VII:

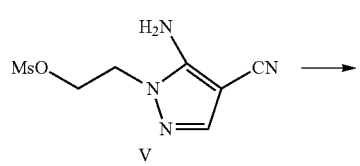

V

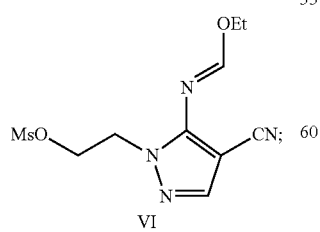

VI (b) condensing imidate VI with 2-butynoylhydrazine p-toluenesulfonate (VII) to obtain the adduct compound VIII:

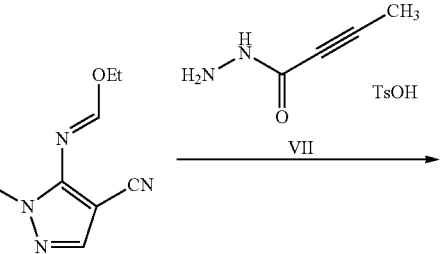

VI

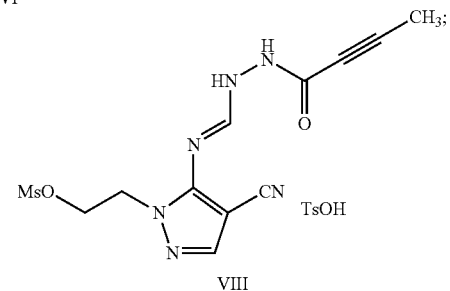

VIII (c) cyclizing and dehydrating compound VIII with N,O-bistrimethylsilyl acetamide to obtain the 2-propynyl-substituted compound IX:

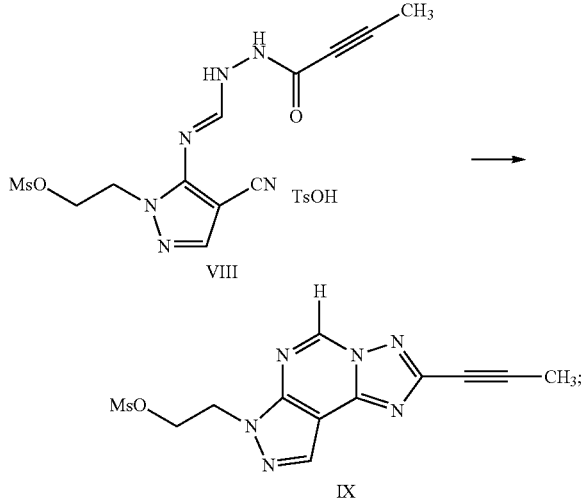

and
(d) hydrolyzing compound IX;
(2) Preparing Compound III

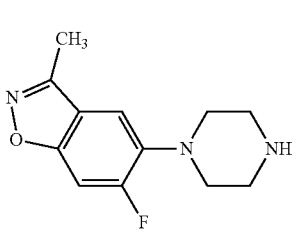

III by (a) reacting 5-amino-6-fluoro-3-methyl-1,2-benzisoxazole (X) with bis(2-chloroethyl)amine in the presence of a base to obtain the compound III:

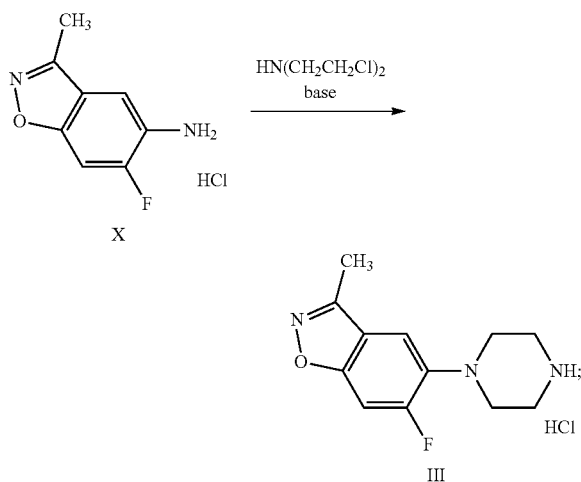

and (b) isolating compound III from the reaction mixture of step (a) by the addition of an anti-solvent; and (3) (i) Condensing Compounds II and III to Obtain the Compound IV

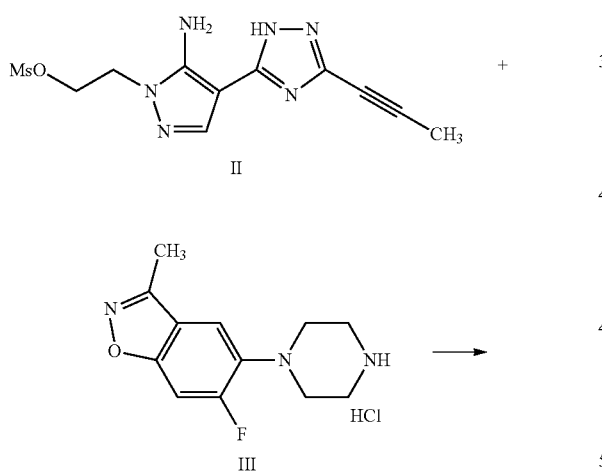

(ii) cyclizing compound IV to obtain compound I; and
(iii) purifying the product of step (ii).

In another embodiment of the invention, the process for preparing the compound of Formula I

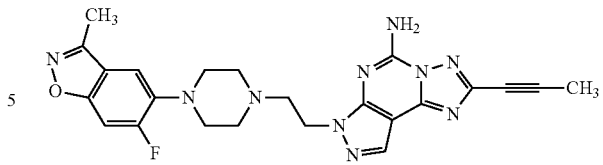

comprises:

(1) Preparing Compound II

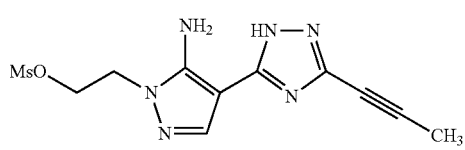 [SMILES: CC#Cc1n[nH]c(-c2cnn(CCOS(C)(=O)=O)c2N)n1]

by (a) treating compound V with triethyl orthoformate to obtain imidate VI:

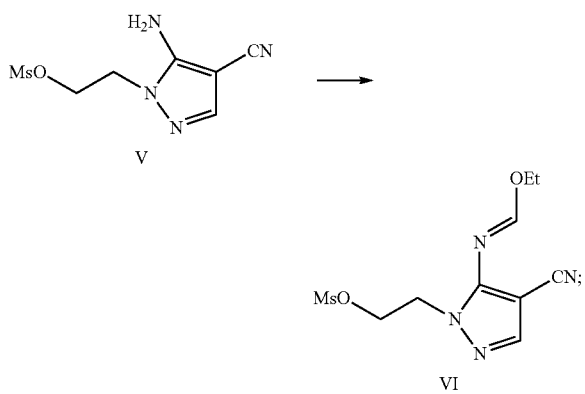

(b) condensing imidate VI with 2-butynoylhydrazine p-toluenesulfonate (VII) to obtain the adduct compound VIII:

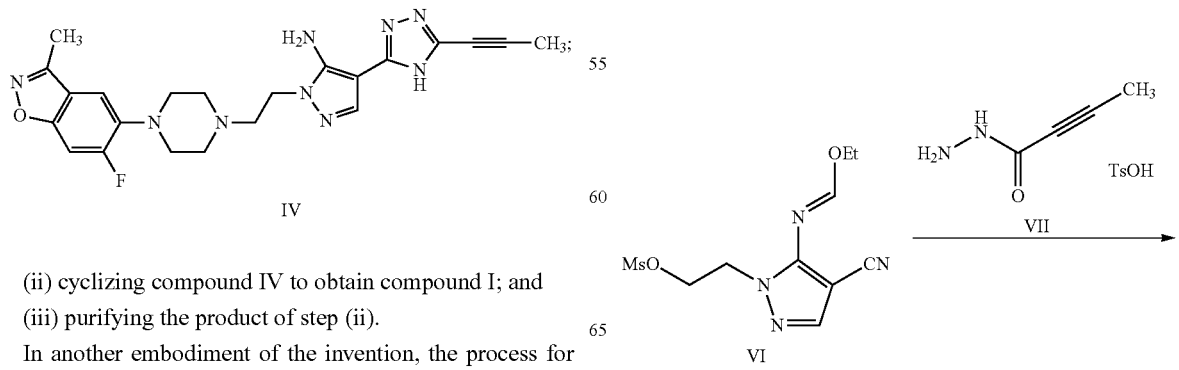

-continued

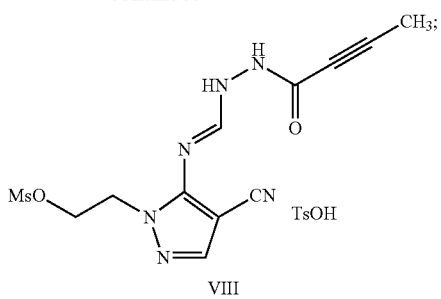

VIII (c) cyclizing and dehydrating compound VIII with N,O-bistrimethylsilyl acetamide to obtain the 2-propynyl-substituted compound IX:

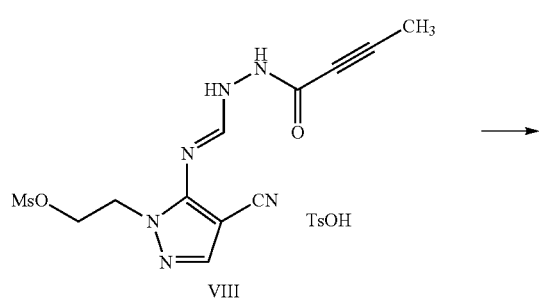

and (d) hydrolyzing compound IX;

(2) Preparing Compound III

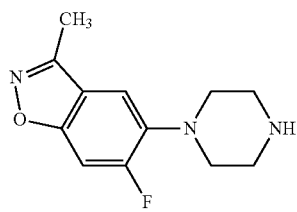

III by (a) treating the acetophenone XII with hydroxylamine hydrochloride to obtain the corresponding oxime (XIII)

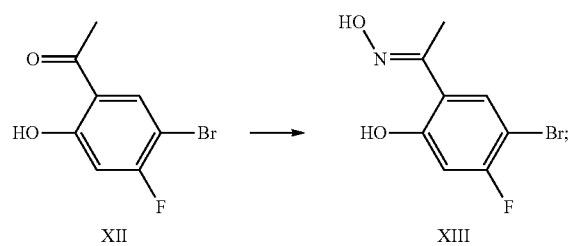

(b) cyclizing the oxime XIII to the benzisoxazole XIV

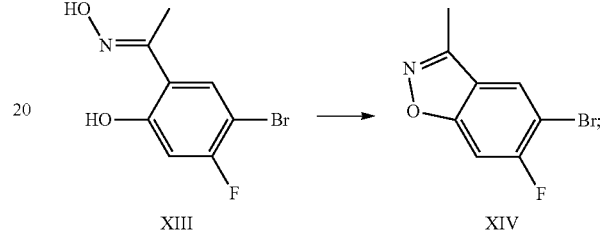

(c) converting the benzisoxazole XIV to an organozinc reagent and coupling it with a protected piperazine in the presence of a copper catalyst to obtain the compound XV

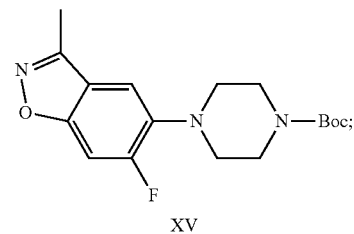

and (d) removing the protecting group on compound XV and converting it to the HCl salt;

and (3) (i) Condensing Compounds II and III to Obtain the Compound IV

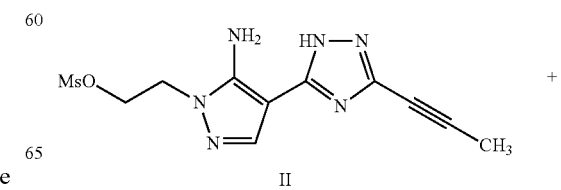

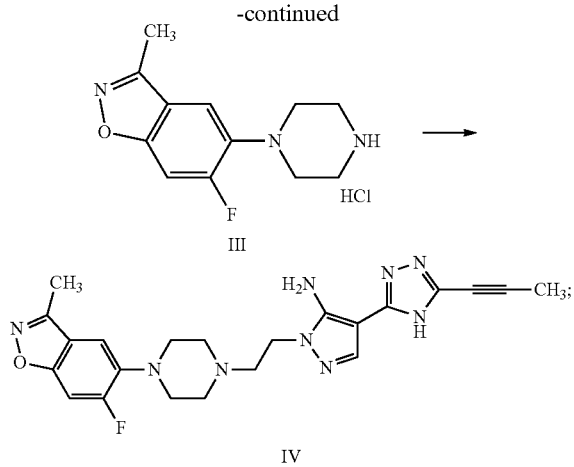

(ii) cyclizing compound IV to obtain compound I; and
(ii) purifying the product of (ii).

Starting materials of formula III, V, X and XII are known in the art; for example, see U.S. Pat. No. 7,223,861, US 2007/0072867, and WO2006083779

In step (i) in the preparation of the compound of formula I, the hydrochloride salt III is converted to the free base by dissolving it an organic solvent such as toluene, then treating it with a base such as aqueous NaOH. The free base of III is then condensed with the propynyl compound II by heating a mixture of II and III in a solvent such as NMP in the presence of an organic base such as DIEA. An antisolvent such as a dilute aqueous solution of $NaHCO_3$ is added to promote crystallization of the desired compound IV.

In step (ii), the compound of formula IV is cyclized by treatment with a cyanating agent such as a cyanate or a cyanogen halide, particularly cyanogen bromide, in the presence of a base such as KOH and/or $K_2HPO_4$. 1-2 equivalents of the cyanating agent are used, preferably about 1.6. The solvent is a mixture of water and an organic solvent such as THF or acetonitrile or a mixture thereof. The reaction is conducted at a temperature range of about 45 to 55° C.

In step (ii), the compound of formula I is purified by recrystallization from an acidic aqueous solution, followed by recrystallization from an alcohol such as ethanol.

The intermediate of formula II is prepared by the following procedure:

In step (a) the amine of formula V is heated to reflux with 1-2 equivalents, preferably 1.2 equivalents, of a trialkylorthoformate, preferably triethyl orthoformate, in a solvent such as isopropyl acetate, and in the presence of a catalytic amount of an organic or inorganic acid, preferably p-toluene sulfonic acid, to form the imidate of formula VI.

In step (b) the imidate of formula VI is condensed with 1-2 equivalents, preferably about 1 equivalent, of a salt of 2-butynoic acid hydrazide, preferably the p-toluene sulfonic acid salt, in a solvent such as acetonitrile. The reaction is carried out at a temperature range of about 30 to 40° C. The product of formula VIII is filtered and can be used without further purification in step (c).

In step (c) the compound of formula VIII is cyclized and dehydrated by heating at 60 to 70° C. with 2-3, preferably about 2.5 equivalents of N,O-bistrimethyl-silylacetamide in a solvent such as NMP to obtain the compound of the formula IX.

In step (d) compound IX is hydrolysed with a dilute aqueous acid, for example with dilute sulfuric acid, in refluxing alcohol, preferably methanol, to obtain crystalline compound II.

The intermediate of formula III is prepared by one of two methods:
Method A:

In step (a) a mixture of 5-amino-6-fluoro-3-methyl-1,2-benzisoxazole (X) is heated with about 2 molar equivalents of bis(2-chloroethyl)amine hydrochloride in a solvent such as NMP in the presence of 1.5-2.5, preferably about 2.1 molar equivalents of a base such as 2,6-lutidine, at a temperature range of about 120 to 130° C. until the reaction is complete, typically about 24 hours;

In step (b) the reaction mixture is cooled and an antisolvent such as ethanol is added to precipitate the compound of formula III.

4:

In step (a), a mixture of 5'-bromo-4'-fluoro-2'-hydroxyacetophenone and hydroxylamine hydrochloride is suspended in an alcohol solvent, such as ethanol, and a suitable base, such as sodium hydroxide, is added. The mixture is heated to reflux temperature (i.e. 80-85° C. for ethanol) and held until the reaction is complete, typically about 1 hour. An antisolvent, such as water, is added, and the solution is cooled slowly to between 0 and 10° C. to crystallize the compound of formula XIII.

In step (b), a mixture of 5'-bromo-4'-fluoro-2'-hydroxyacetophenone oxime, anhydrous inorganic base, such as potassium or sodium carbonate, and acetic anhydride is suspended in a suitable organic solvent, such as toluene or N-methyl-1-pyrrolidinone. The mixture is heated to between 90 and 100° C. and held until the reaction is complete, typically about 2 hours. After aqueous washing, the product is crystallized from an organic solvent mixture of tert-butyl methyl ether and hexanes to afford the compound of formula XIV.

In step (c), an organozinc reagent is prepared from 5-bromo-6-fluoro-3-methylbenzo[d]isoxazole (XIV) by dissolving it in an anhydrous solvent such as THF, cooling to a temperature of about −10 to 0° C., preferably about −5° C., and reacting it with about 1-2 molar equivalents, preferably about 1.2 equivalents of a gringard reagent such as iPrMgCl—LiCl, and combining the mixture with anhydrous $ZnCl_2$. The resulting compound is reacted with about 1 to 1.5, preferably about 1.1 equivalents of 1-benzoyloxy-4-(1,1-dimethylethoxycarbonyl)piperazine (prepared as described in U.S. Pat. No. 4,247,549) in an anhydrous solvent such as THF in the presence of a catalytic amount of a copper catalyst such as $Cu(OTf)_2$; the reaction is carried out at 20 to 30° C., preferably 25° C., until the reaction is complete, typically about 1 hour, to obtain compound XV.

In step (d), the protected nitrogen of compound XV is deprotected and converted to a salt, preferably the HCl salt, by treating compound XV with aqueous acid, preferably HCl, in an alcohol, preferably ethanol, to obtain compound III.

The present process provides an advantage over the procedures previously reported in the art.

Compared to processes known in the art, the presently claimed processes for preparing intermediate compound II and reacting it with intermediate compound III to prepare the compound of formula I has fewer synthetic steps, reduces solvent usage and eliminates silica gel column chromatography purification.

Method A for the preparation of compound III significantly improves the yield compared to known methods. The use of a base is unexpected in this type of piperazine ring closure, and the use of the antisolvent allows direct isolation of the product in high purity from the reaction mixture while eliminating the aqueous workup and silica gel column chromatography required in previously known methods.

Method B for the preparation of compound III is a novel synthesis for aryl piperazines which avoids the use of bis-(2-chloroethyl)amine hydrochloride, a suspect carcinogen.

The following abbreviations are used in the specification and claims: Ms (methylsulfonyl); Boc (N-tert-butoxycarbonyl); DMSO (dimethyl sulfoxide); BSA (N,O-Bis(trimethylsilyl)acetamide); NMP (N-methyl-pyrrolidinone); Pr (propyl); Ph (phenyl); THF (tetrahydrofuran); DIEA (N,N-diisopropylethylamine; and $Cu(OTf)_2$ (copper (II) trifluoromethanesulfonate).

Following are descriptions of the preparation of the compound of Formula I using the claimed processes.

Preparation of II

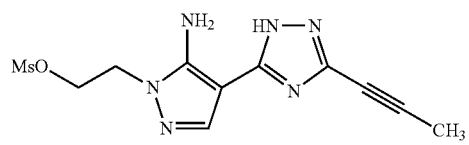

Step (a):

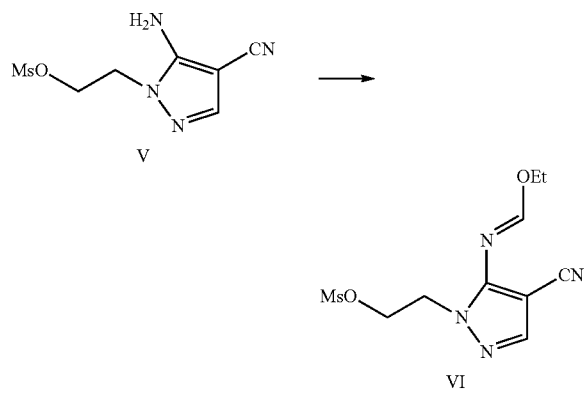

Compound V (5-Amino-1-[2-[(methylsulfonyl)oxy]ethyl]-1H-pyrazole-4-carbonitrile) (80.0 kg, 347.5 moles), prepared as described in U.S. Pat. No. 7,223,861, was combined with triethyl orthoformate (56.8 kg, 383.3 moles, 1.1 molar equivalents) in isopropyl acetate (400 L) with a catalytic amount of p-toluenesulfonic acid monohydrate (0.2 kg, 1.05 moles, 0.003 molar equivalents). The resulting mixture was heated to reflux, and the ethanol byproducts were azeotropically distilled out of the reaction mixture. After the azeotropic distillation was complete, the batch was cooled to 50-60° C. and sampled for completion (≤5% compound VI remained by HPLC). The batch was then diluted with t-Butyl Methyl Ether and cooled to between 35 and 45° C. 0.004× of seed crystals of compound VII were introduced. The batch was agitated for 3 hours between 35 and 45° C. and then cooled to between 5 and 15° C. over 1 hour and held for 1 hour between 5 and 15° C. The product was isolated by filtration, washed with a solvent mixture of isopropyl acetate and t-Butyl Methyl Ether, and dried at a temperature between 35 and 45° C. for at least 4 hours. The typical molar yield was between 85 and 95%. $^1$H NMR (CDCl$_3$, ppm): 1.42 (t, 3H, J=7 Hz); 2.93 (s, 3H); 4.41 (m, 4H); 4.43 (m, 2H); 7.68 (s, 1H); 8.69 (s, 1H).

Steps (b) and (c):

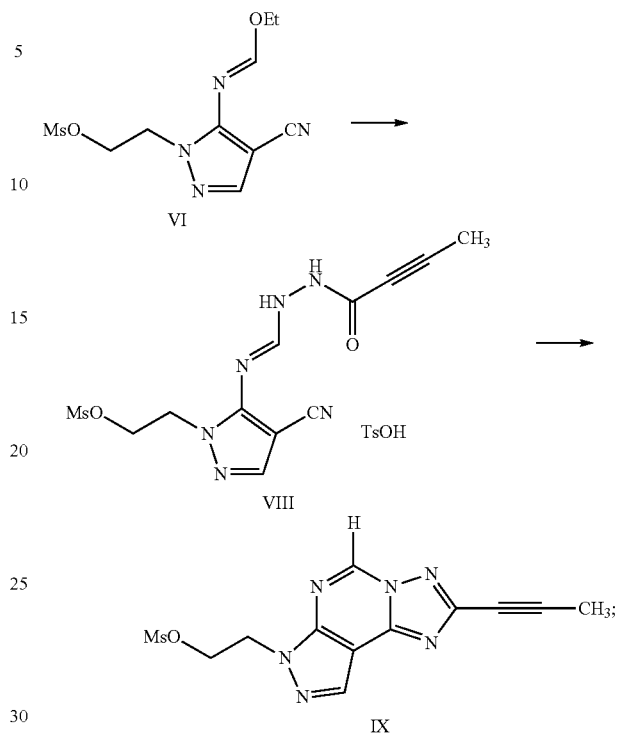

Ethyl [4-cyano-1-[2-[(methylsulfonyl)oxy]ethyl]-1H-pyrazol-5-yl]methanimidate (VI) (75.0 kg, 262.0 moles) was coupled with 2-butynoic acid hydrazide p-toluenesulfonic acid salt (VII) (75.0 kg, 277.5 moles, 1.06 molar equivalents) in acetonitrile (750 L) between 30 and 40° C. for 5 hours. The batch was cooled to between 0 and 10° C. and the coupling product, 2-butynoic acid, 2-[(E)-[[4-cyano-1-[2-[(methylsulfonyl)oxy]-ethyl]-1H-pyrazol-5-yl]imino]methyl]hydrazide, 4-methylbenzenesulfonate (VII), was filtered. The crude product was charged back to the reactor, dissolved in NMP (225 L) then treated with BSA (139.9 kg, 687.7 moles, 2.5 molar equivalents) between 60 and 70° C. for 3 hours. The reaction mixture was cooled to between 0 and 10° C. then quenched with water (600 L) to affect the precipitation. The product IX was filtered, washed with water (225 L) and dried at a temperature between 40 and 50° C. The typical molar yield was between 50 to 70%. $^1$H NMR (d$_6$-DMSO, ppm): 2.21 (s, 3H); 3.10 (s, 3H); 4.75 (m, 2H); 4.89 (m, 2H); 8.60 (s, 1H); 9.65 (s, 1H).

Step (d):

2-(1-Propynyl)-7H-pyrazolo[4,3-e][1,2,4]triazolo[1,5-c]pyrimidine-7-ethanol, methanesulfonate ester (IX) (53.0 kg, 165.5 moles) was hydrolyzed with dilute sulfuric acid (46% v/v, 9.24 L, 83.2 moles, 0.5 molar equivalents) in refluxing methyl alcohol (185.5 L) at a temperature between 60 and 65° C. over 4 hours. Once the reaction was complete, the batch was cooled to between 15 and 25° C. In a separate vessel, water (848 L) was heated to between 40 and 50° C., and the reaction mixture was transferred into the pre-heated water. The product began to crystallize during transfer. The batch was then cooled to between 0 and 10° C. over 4 hours. After agitating for an additional hour, the product was isolated by filtration and washed with a cooled (between 0 and 10° C.) 20% methyl alcohol in water solution (265 L). The product was dried in a vacuum oven between 50 and 60° C. for at least 12 hours. The typical molar yield was between 70 and 90% as the crystalline monohydrate. $^1$H NMR (d$_6$-DMSO, ppm): 2.10 (s, 3H); 3.11 (s, 3H); 3.40 (s, br, 2H); 4.33 (m, 2H); 4.54 (m, 2H); 6.23 (s, br, 2H); 14.16 (s, br, 1H).

Preparation of III

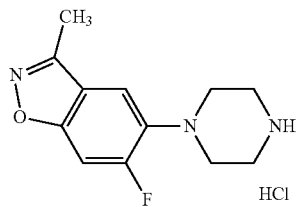

III

Method A
Step (a):

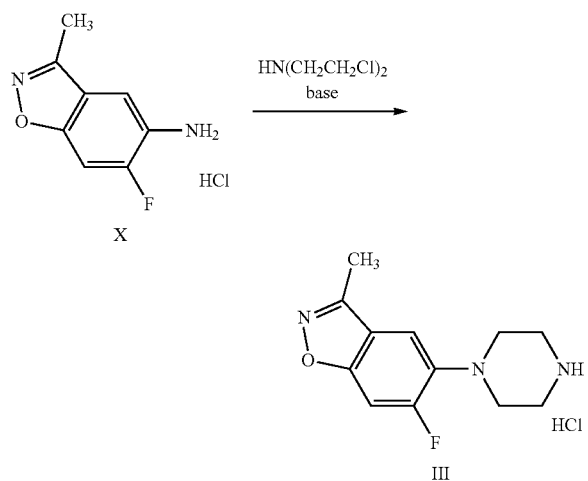

5-Amino-6-fluoro-3-methylbenzo[d]isoxazole hydrochloride (X) (65.0 kg, 320.8 moles), bis(2-chloroethyl)amine hydrochloride (114.4 kg, 640.9 moles, 2.0 molar equivalents), NMP (335.4 kg), water (13 L) and 2,6-lutidine (71.5 kg, 667.2 moles, 2.1 molar equivalents) were charged to the reactor while maintaining the temperature between 20 and 30° C. The batch was heated to between 120 and 130° C. and agitated at this temperature for 24 hours. The reaction was sampled for completion.

Step (b):

Once the desired conversion was reached, the batch was cooled to between 70 and 80° C. and ethanol (424.3 kg) was added. The batch was further cooled to between 0 and 10° C. and agitated for 1 hour, filtered, and washed with ethanol (106.0 kg). The crude wet cake was slurried in ethanol (530.4 kg) between 20 and 30° C. for 1 hour and filtered. The product was dried in a vacuum oven between 40 and 50° C. Typical molar yield was between 45 and 60% as the hydrochloride salt. $^1$H NMR (d$_6$-DMSO, ppm): 9.47 (s, br, 2H), 7.71 (d, J=11.6 Hz, 1H), 7.56 (d, J=8.2 Hz, 1H), 3.24 (m, 8H), 2.51 (m, 3H)

Method B
Step (a):

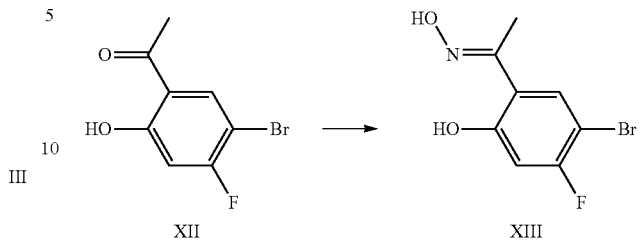

5'-bromo-4'-fluoro-2'-hydroxyacetophenone (5.50 g, 23.6 mmol), hydroxylamine hydrochloride (2.00 g, 28.3 mmol), and ethanol (33 mL) were charged to a reaction flask. NaOH (1.1 g, 28.3 mmol) was added slowly while maintaining the reaction at a temperature less than 50° C. After the addition was completed, the reaction mixture was gradually heated to reflux (80 to 85° C.) and held for 1 hour, or until all the starting material was consumed. Water (77 mL) was added, and the solution was cooled slowly to between 0 and 10° C. After stirring an additional hour, the product was filtered and the filtrate was used to wash the reaction flask and product cake. Water (22 mL) was subsequently used to wash the reaction flask and product cake. The product was then dried in a vacuum oven between 30 and 50° C. for at least 12 hours, or until the product (compound XIII) was dry. Typical molar yield was between 90-95%. $^1$H NMR (400 MHz, CDCl$_3$) δ 11.46 (d, 1H), 7.56 (d, J=7.6 Hz, 1H), 7.39 (s, 1H), 6.75 (d, J=9.9 Hz, 1H), 2.33 (s, 3H).

Step (b)

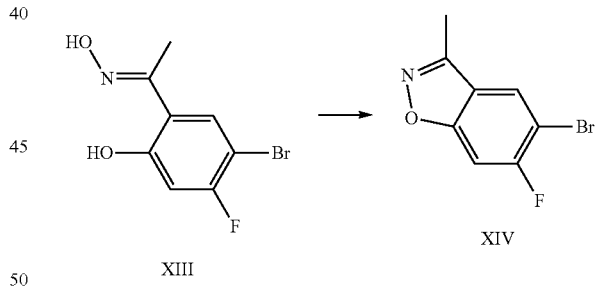

The product of Step (a) (XIII) (13.0 g, 52.4 mmol) and K$_2$CO$_3$ (4.3 g, 31.4 mmol) were charged to a reaction flask. NMP (55 mL) was added followed by acetic anhydride (5.4 mL, 57.7 mmol). The resulting mixture was heated to 90-100° C. and held for 1-2 hours, or until all the starting material was consumed. The reaction mixture was cooled to 25° C. Water (13 mL) and methyl tert-butyl ether (104 mL) were added. The product was extracted to the organic layer, which was further washed by water (26 mL) twice. The organic layer was concentrated under vacuum to about 1.5× (20 mL) volume. Heptanes (65 mL) was added to the batch and the mixture was concentrated to about 3× (40 mL). The batch was cooled to 0-5° C. to crystallize the product (XIV). Typical molar yield was between 80-85%. $^1$H NMR (400 MHz, CDCl$_3$) δ 7.87 (d, J=6.4 Hz, 1H), 7.34 (d, J=7.9 Hz, 1H), 2.57 (s, 3H).

Step (c):

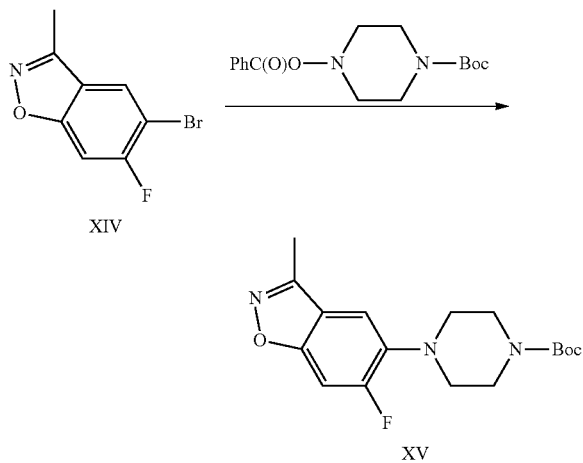

5-bromo-6-fluoro-3-methylbenzo[d]isoxazole (XIV) (230 mg, 1.0 mmol) was dissolved in anhydrous THF (5 mL) under dry nitrogen. The solution was cooled to −5° C., and the Grignard reagent iPrMgCl—LiCl (0.828 mL, 1.20 mmol) was added over 1 hour. In a separate vessel, anhydrous ZnCl$_2$ (75 mg, 0.55 mmol) was dissolved in anhydrous THF (1 mL) at 25° C. under dry nitrogen. The Grignard solution was transferred via cannula to the zinc solution and the mixture was stirred at 25° C. for 30 min. In a separate vessel, 1-benzyloxy-4-(1,1-dimethylethoxycarbonyl)piperazine (337 mg, 1.10 mmol) and Cu(OTf)$_2$ (36 mg, 0.1 mmol) were dissolved in anhydrous THF (2 mL) at 25° C. The Grignard/zinc solution was transferred via cannula to the oxypiperazine solution and the mixture was stirred for 30 min. Sampling the reaction by HPLC analysis showed 83% conversion. After 1 hour, the reaction was quenched with water (10 mL). The reaction mixture was extracted with ethyl acetate (3×15 mL), washed with 5% brine solution (5 mL), dried over MgSO$_4$ and filtered through a celite cake. The solution was concentrated to an oil under vacuum. The crude product was purified by flash column chromatography (ethyl acetate/hexane=1:3) with silica gel to give the product (XV) as a white solid (250 mg, 75% yield). $^1$H NMR (CDCl$_3$, ppm): 7.26 (d, J=11.1 Hz, 1H), 7.08 (d, J=7.8 Hz, 1H), 3.63 (m, 4H), 3.00 (m, 4H), 2.54 (m, 3H), 1.50 (s, 9H).

Step (d):

The product of Step (d) (XV) was deprotected with aqueous hydrochloric acid in ethyl alcohol to afford III.

Preparation of IV

IV

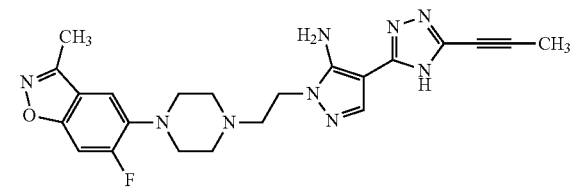

6-fluoro-3-methyl-5-piperazin-1-ylbenzo[d]isoxazole hydrochloride (III) (39.7 kg, 146.1 moles, 1.2 molar equivalents) was converted into the free based by adding an aqueous NaOH (80 L) solution of III to toluene (320 L) in the presence of celite (3.2 kg). The mixture was filtered, the layers were separated, and the organic layer was washed with NaCl solution. The free base solution was then concentrated by vacuum distillation. To the solution was charged 2-[5-amino-4-(3-prop-1-ynyl-1H-1,2,4-triazol-5-yl)-1H-pyrazol-1-yl]ethyl methanesulfonate monohydrate (II) (40.0 kg, 121.8 moles), followed by NMP (116 kg), and then DIEA (11.8 kg). The solution was heated to between 65 and 75° C. and agitated for 2 hours. The temperature was adjusted to between 75 and 85° C., additional DIEA (11.8 kg) was charged, and mixing was continued for 2 more hours. The temperature was then adjusted to between 85 and 95° C., and mixing was continued for 2 additional hours. The temperature was adjusted to between 105 and 115° C., and mixing was continued for 6 additional hours. The reaction was cooled and sampled for completion. The solvent was removed by vacuum distillation. The temperature was adjusted to between 65 and 75° C., and a dilute solution of aqueous NaHCO$_3$ was added as an antisolvent. The batch was cooled to between 35 and 45° C., during which time the product (IV) crystallized. Additional bicarbonate solution was slowly added, and then the batch was cooled to between 0-10° C. and held for 2 hours. The product was recovered by filtration and washed with a water/methanol solution, followed by water. The wet cake was dried in a vacuum dryer between 35 and 45° C. for at least 14 hours. Typical molar yield was between 70 and 90%. $^1$H NMR (d$_6$-DMSO, ppm): 2.05 (s, 3H); 2.50 (s, 3H), 2.65 (s, br, 4H); 2.72 (m, 2H); 3.00 (s, br, 4H); 4.10 (m, 2H); 6.19 (s, br, 2H); 7.45 (m, 1H); 7.62 (m, 2H); 13.85 (s, br, 1H).

Preparation of I

I

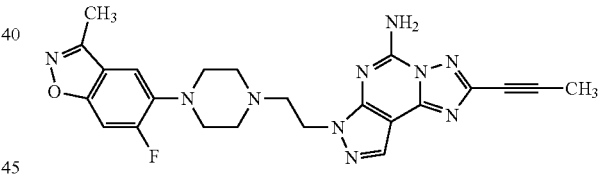

1-[2-[4-(6-Fluoro-3-methyl-1,2-benzisoxazol-5-yl)-1-piperazinyl]ethyl]-4-[5-(1-propynyl)-4H-1,2,4-triazol-3-yl]-1H-pyrazol-5-amine (IV) (26.0 kg, 57.8 moles) was charged to a reactor containing potassium phosphate, dibasic (62.4 kg, 358.3 moles, 6.0 molar equivalents), KOH (10.1 kg, 180.0 moles, 3.1 molar equivalents) and water (130 L). THF (130 L) was added and the solution was heated to between 45 and 55° C. A solution of cyanogen bromide in acetonitrile (50% w/w, 19.9 kg, 93.9 moles, 1.6 molar equivalents) was added over at least 30 minutes while maintaining the temperature between 45 and 55° C. The product (I) began to crystallize out of the reaction mixture during the addition. The resulting mixture was agitated for at least 2 hours while maintaining the temperature between 45 and 55° C. After sampling for reaction completion (I≤3.0% by area normalization), the mixture was cooled to between 15 and 25° C. over at least 1 hour and agitated for at least 2 hours. The product was filtered and washed with water (130 L). The wet cake was returned to the reactor and reslurried in a solution of THF (130 L) and water (130 L) at a temperature between 45 and 55° C. for at least 6 hours. The mixture was cooled to between 15 and 25° C. over at least 1 hour and agitated for at least 2 hours. The product was filtered and washed sequentially with THF (52 L) then water (52 L). The product cake was dried in a vacuum oven at a temperature between 45 and 55° C. for at least 18 hours. The typical molar yield was between 70 and 90%. $^1$H NMR (d$_6$-DMSO, ppm): 2.12 (s, 3H); 2.48 (s, 3H); 2.63 (s, br, 4H); 2.84 (t, 2H, J=6.7 Hz); 2.92 (m, br, 4H); 4.40 (t, 2H, J=6.7 Hz); 7.37 (d, 1H, J=8.2 Hz); 7.61 (d, 1H, J=11.6 Hz); 8.06 (s, br, 2H); 8.10 (s, 1H).

Preparation of Purified I

7-[2-[4-(6-fluoro-3-methyl-1,2-benzisoxazol-5-yl)-1-piperazinyl]ethyl]-2-(1-propynyl)-7H-pyrazolo[4,3-e][1,2,4]triazolo[1,5-c]pyrimidin-5-amine (I) (30.4 kg, 64.1 moles) was dissolved in a solution of water (15.2 L) and acetic acid (211.5 kg) by agitating for at least 1 hour while maintaining the temperature between 20 and 30° C. The solution was decolorized by passing through a cartridge of activated carbon, then filtered through a 0.2 micron in-line filter. The resulting solution was heated to between 55 and 65° C. Water (152 L) was added slowly over 1 to 2 hours while maintaining the temperature between 55 and 65° C. to begin to crystallize the product. The mixture was aged for 2 hours. A second portion of water (486 L) was charged over 2 to 3 hours while maintaining the temperature between 55 and 65° C. The resulting slurry was cooled slowly over 4 to 6 hours to a temperature between 10 and 20° C. After agitating for an additional 2 hours, the product was filtered, and the wet cake was washed with ethyl alcohol (240.0 kg). The wet cake was returned to the reactor and reslurried in ethyl alcohol (479.7 kg) at a temperature between 55 and 65° C. for at least 2 hours to obtain the desired crystal form. The mixture was then cooled to between 10 and 20° C. and agitated for at least 1 hour. The product was isolated by filtration and washed with ethyl alcohol (118.6 kg). The isolated cake was dried in a vacuum oven at a temperature between 30 and 40° C. The typical molar yield was between 85 and 95%. $^1$H NMR (d$_6$-DMSO, ppm): 2.12 (s, 3H); 2.48 (s, 3H); 2.63 (s, br, 4H); 2.84 (t, 2H, J=6.7 Hz); 2.92 (m, br, 4H); 4.40 (t, 2H, J=6.7 Hz); 7.37 (d, 1H, J=8.2 Hz); 7.61 (d, 1H, J=11.6 Hz); 8.06 (s, br, 2H); 8.10 (s, 1H).

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A process for preparing the compound having the structural Formula I:

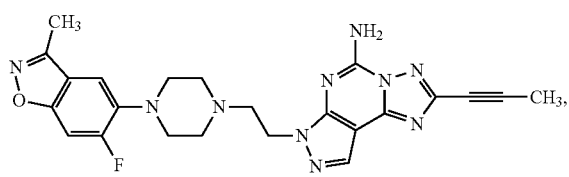

comprising:
(i) preparing a compound of Formula II:

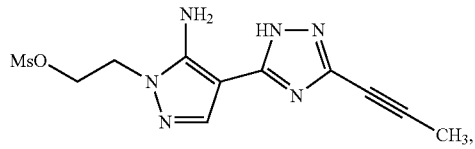

using a process comprising:
(a) treating a compound V with triethyl orthoformate to obtain imidate VI:

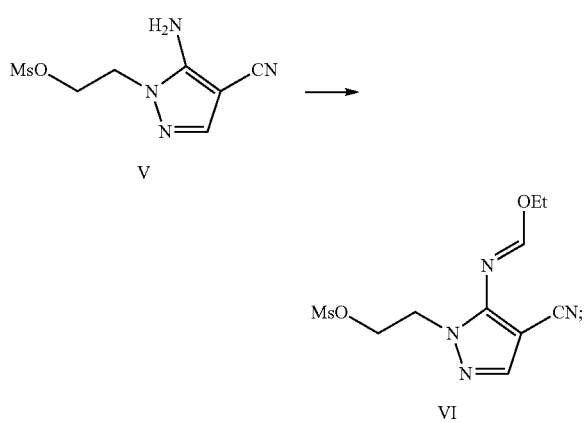

(b) condensing imidate VI with 2-butynoylhydrazine p-toluenensulfonate (VII) to obtain the adduct compound VIII:

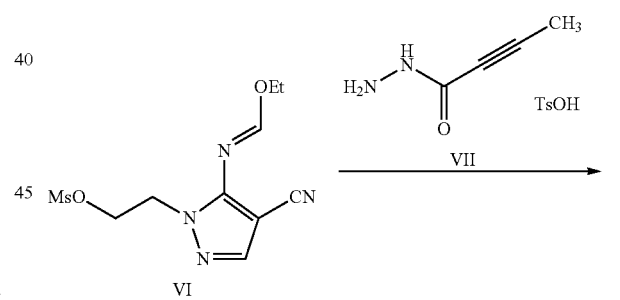

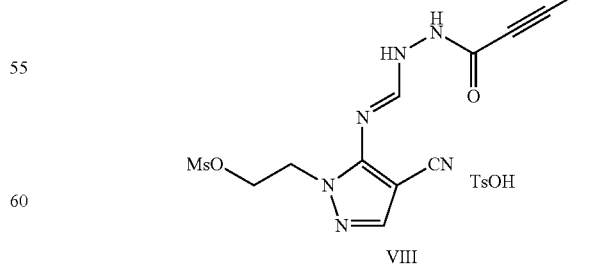

(c) cyclizing and dehydrating compound VIII with N,O-bistrimethylsilyl acetamide to obtain the 2-propynyl-substituted compound IX:

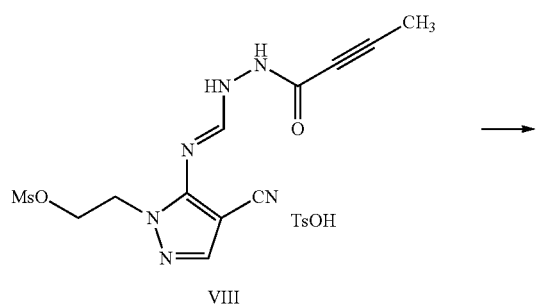

VIII

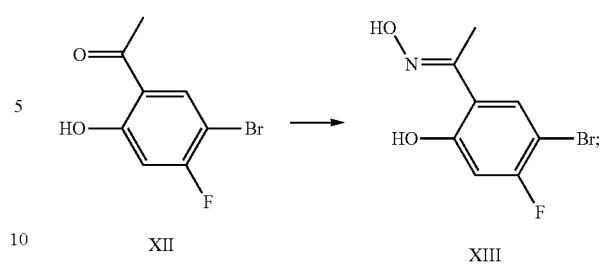

XII → XIII (b) cyclizing the oxime XIII to the benzisoxazole XIV

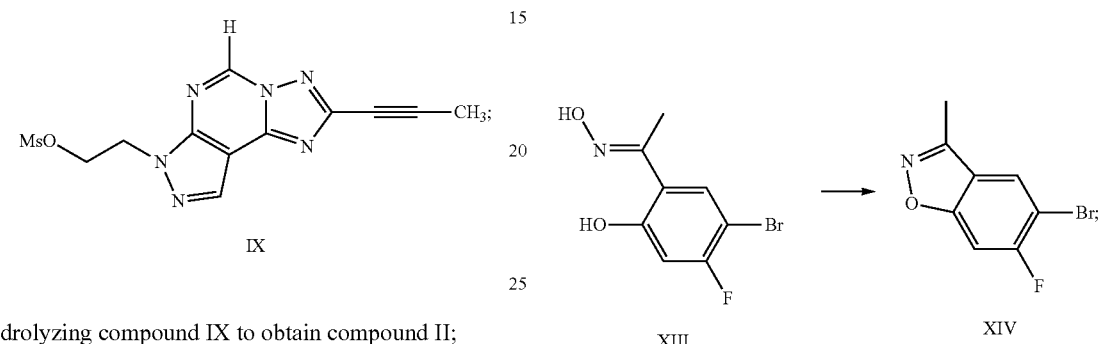

IX and
(d) hydrolyzing compound IX to obtain compound II;
(ii) condensing compound II with compound III to obtain compound IV

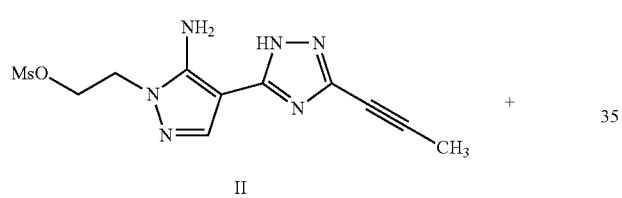

II

XIII → XIV (c) converting the benzisoxazole XIV to an organozinc reagent and coupling it with a protected piperazine in the presence of a copper catalyst to obtain the compound XV,

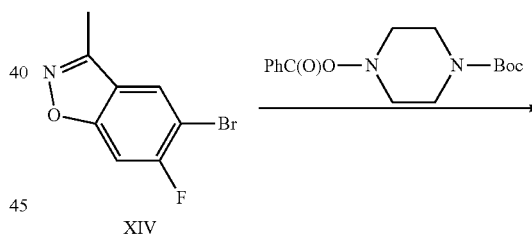

III

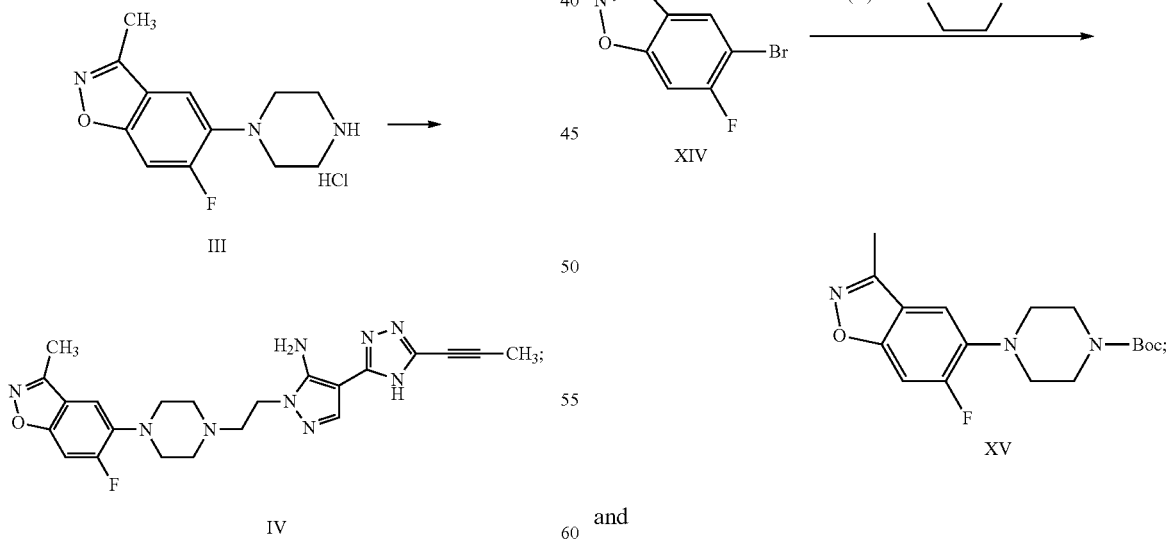

IV (iii) cyclizing compound IV to obtain compound I; and
(iv) optionally purifying the product of step (iii).

2. The process of claim 1 wherein said compound of Formula III is provided to the process by:

(a) treating the acetophenone XII with hydroxylamine hydrochloride to obtain the corresponding oxime (XIII)

and
(d) removing the protecting group on compound XV and converting it to the HCl salt.

3. The process of claim 1 wherein said compound of Formula III is provided to the process by reacting 5-amino-6-fluoro-3-methylbenzo[d]-isoxazole (X) with bis(2-chloroethyl)amine in the presence of a base to obtain the compound of Formula III:

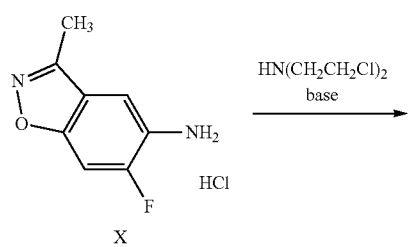
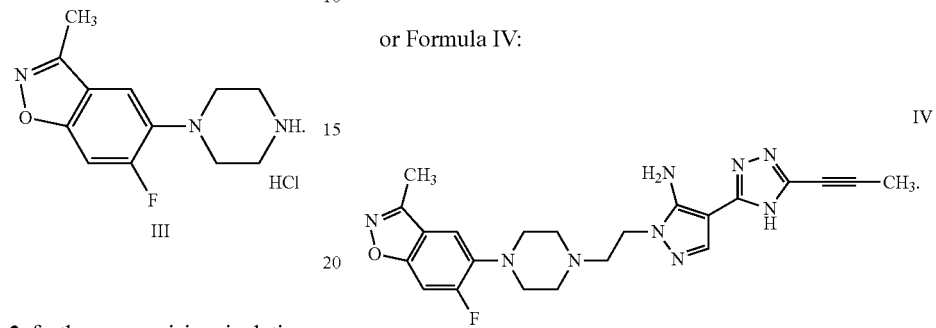
4. The process of claim 3 further comprising isolating compound III from the reaction mixture by the addition of an anti-solvent.
5. A compound of Formula II:
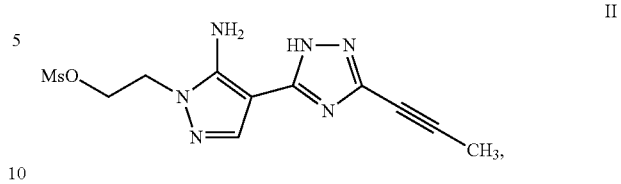
or Formula IV:
* * * * *